United States Patent [19]

Tai

[11] Patent Number: 5,090,807
[45] Date of Patent: Feb. 25, 1992

[54] REAL TIME OPTICAL PRE-DETECTION PROCESSING OF MULTISPECTRAL IMAGE DATA

[75] Inventor: Anthony M. Tai, Northville, Mich.

[73] Assignee: Environmental Research Institute of Michigan, Ann Arbor, Mich.

[21] Appl. No.: 463,277

[22] Filed: Jan. 10, 1990

[51] Int. Cl.$^5$ ............................................ G01J 3/04
[52] U.S. Cl. .................................. 356/310; 356/330
[58] Field of Search ............... 356/310, 330, 326, 328, 356/327, 331, 334, 330; 250/338.1, 339, 226

[56] References Cited

U.S. PATENT DOCUMENTS 3,314,327  4/1967  Killpatrick et al. ................. 356/310
4,790,654  12/1988  Clarke .................................. 356/310

OTHER PUBLICATIONS

Crist et al., "A Physically Based Transformation of Thematic Mapper Data—The T.M. Cap," IEEE Transactions on Geoscience and Remote Sensing, vol. GE-22, #3, May 1984.

*Primary Examiner*—F. L. Evans
*Assistant Examiner*—K. P. Hantis
*Attorney, Agent, or Firm*—Krass & Young

[57] ABSTRACT

The present invention is an apparatus for forming a spectrally weighted value from received multispectral radiation. The spectral weighting is done optically prior to detection of the received radiation by dispersing the received multispectral radiation into a plurality of wavelength bin areas. This dispersed radiation is then passed through a weighting filter which includes first and second filter elements for each of the wavelength bin areas. The filtered radiation is then converged to corresponding detectors with the spectrally weighted value formed by the difference between the signals of the first and second detectors. A pair of filters, two detectors and a subtracter are employed to produce a generalized weight factor having positive or negative weights. This system can form one or more spectrally weighted values from the radiation from a single pixel, or one spectrally weighted value form the radiation from a plurality of pixels. The addition of a polarization filter permits the formation of spectrally weighted values for various polarizations of a single pixel.

11 Claims, 4 Drawing Sheets

REAL TIME OPTICAL PRE-DETECTION PROCESSING OF MULTISPECTRAL IMAGE DATA

This invention was made with Government support under Contract F30602-87-C-0012 awarded by Rome Air Development Center, Department of the Air Force. The Government has certain rights in this invention.

TECHNICAL FIELD OF THE INVENTION

The technical field of the invention is that of spectral image processing, and more particularly optical pre-detection processing of multispectral image data.

BACKGROUND OF THE INVENTION

The present invention is useful in the field of image processing. Substantial information regarding a scene can be obtained by utilizing the spectral content of the scene. Spectral image processing is advantageous in satellite land use surveys and in target identification in a cluttered scene.

In the field of land use analysis, it is known to employ spectral analysis of reflected ambient radiation received by a moving platform. It is typical to use a technique called "push broom" in which an aircraft or satellite employs a sensor for viewing a number of cross track pixels and the motion of the platform scans this viewed region along the track of motion. It is known in the art to employ linear combinations of spectral bands of the received data to form dimension reduced characteristics. The characteristics of any particular pixel can be plotted on a graph of such characteristics permitting land use classification by its spectral character as taught by E.P. Christ and R.C. Cicone, "A Physically Based Transformation of Thematic Mapper Data - The TM Tasseled Cap," IEEE Trans. on Geoscience and Remote Sensing, Vol. GE-22, No. 3, pp. 256-263 (1984).

In addition, analysis of the spectral character of a pixel can aid in target classification. It is known that certain target types have spectral characteristics which permit identification and classification. A further use of spectral analysis includes enhancement of target spectral characteristics while simultaneously suppressing known background clutter characteristics. This technique has the potential for greatly improving the capability of target detection.

In order to perform such spectral analysis, it is necessary to produce a spectrally weighted value or values from the electromagnetic radiation received from the area of interest. This process can be performed by detection of the radiation intensity using an electronic detector, followed by electronic analysis of this signal. The processing can be carried out using a digital computer. In general, however, the amount of processing required for the solution of many practical problems in real time is beyond the capability of any present or proposed future computer system. Thus either the benefit of this technique is lost or the processing must take place after the scene detection at the slower rate of the processing system.

Therefore there is a need in the art for a manner of producing one or more spectrally weighted values from the radiation received from a pixel of interest in real time at the rate of pixel imaging.

SUMMARY OF THE INVENTION

The present invention is an apparatus for forming a spectrally weighted value from received multispectral radiation. In accordance with the present invention the spectral weighting is done optically prior to detection of the received radiation. The received multispectral radiation is passed through a wavelength dispersing element for spatially disbursing the received radiation by wavelength into a plurality of wavelength band areas. This dispersed radiation is then passed through a pair of weighting filters representing the positive and negative weights. In the preferred embodiment, the weighting filter is a transmission filter including regions with selected transmittance corresponding to the desired weights. Alternatively, the weighting filter could be a reflection filter having regions with selected reflectivity corresponding to the desired weights. The essential feature is that the filter pass a portion of the incident radiation.

The filtered radiation is then passed through a wavelength converging element. This wavelength converging element is the inverse of the wavelength dispersing element. The wavelength converging element assembles the radiation from the various wavelength band areas to corresponding detectors. The radiation filtered by the first filter elements are converged on a first detector and the radiation filtered by the second filter elements are converged on a second detector. The bipolar spectrally weighted value is formed by the difference between the signals of the first and second detectors.

Two sets of filters and two detectors are employed to produce a generalized weight factor. In general it would be desirable to permit both positive and negative weights for the spectrally weighted value. Negative weights cannot be realized using transmittance or reflectivity filters. This limitation is overcome using one set of filters for positive weights and one set of filters for negative weights. The positively weighted spectrum is detected at the first detector. The negatively weighted spectrum is detected at the second detector. The difference between these detected signals forms the spectrally weighted value capable of having both positive and negative weights. The result is that the weight for a particular wavelength band area is the difference between the positive filter factor for that wavelength band area and the negative filter factor for that wavelength band area.

The weighting filter can be embodied in two forms. If the desired spectrally weighted values are constant, then the weighting filter consists of a passive transmittance filter having a fixed transmissibility for both positive and negative weights for each wavelength band area. If the desired spectral weights are to be adaptive or not constant, then the weighting filter consists of some form of spatial light modulator. There are numerous types of spatial light modulators known in the art. These types include both transmission and reflection spatial light modulators and include both optically addressed and electronically addresses spatial light modulators.

It is considered advantageous that the wavelength dispersing element and the wavelength converging element be identical, reciprocal devices. These devices can be either prisms or diffraction gratings depending upon the wavelengths involved.

In the preferred embodiment, the apparatus includes focussing and collimating optics with the weighting transmission filter located at an intermediate focal plane.

This technique can be used in a number of alternative embodiments. In a first alternative embodiment, the radiation received from a single pixel is dispersed to a single set of positive and negative filters for a plurality of wavelength areas. This permits the real time computation of a single spectrally weighted value for this single pixel. In a second alternative embodiment, several spectrally weighted values can be formed simultaneously. This required that the spectrally dispersed radiation is further dispersed into a plurality of pairs of weighted value areas for each of the plurality of wavelength band areas. The weighting filter includes properly aligned first and second filter elements for each weighted value area of each wavelength band area. The wavelength converging element converges the filtered radiation to positive and negative detectors for each weighted value area of each wavelength band area. Each pair of positive and negative weight detectors supplies a difference device which forms the corresponding spectrally weighted value.

In a further alternative embodiment, a spectrally weighted value can be simultaneously produced for each of a plurality of pixels. In this embodiment, the wavelength dispersing element spatially disperses the received radiation by wavelength for each of a plurality of pixels into a plurality of wavelength band areas forming a grid. The weighting filter includes positive and negative filter elements for each of the pixels of each wavelength band area. The wavelength converging element spatially converges all wavelengths of radiation filtered by the weighting filter to a linear array of pairs of positive and negative weight detectors. The actual spectrally weighted values are produced electrically from the differences between detectors of these pairs.

In a yet further embodiment, plural spectrally weighted polarization values can be produced. This involves the use of a polarization filter as well as the weighting filter. The polarization filter can have the polarization of the desired signal. In the case that the desired polarization signal is unknown prior to analysis, the polarization filter can have separate sections with differing polarizations, such as 0°, 120° and 240° with respect to a reference direction.

BRIEF DESCRIPTION OF THE DRAWINGS

These and other objects and aspects of the present invention will become clear from the following description of the intention taken together with the drawings, in which.

DETAILED DESCRIPTION OF THE PREFERRED EMBODIMENT

Figure 1:
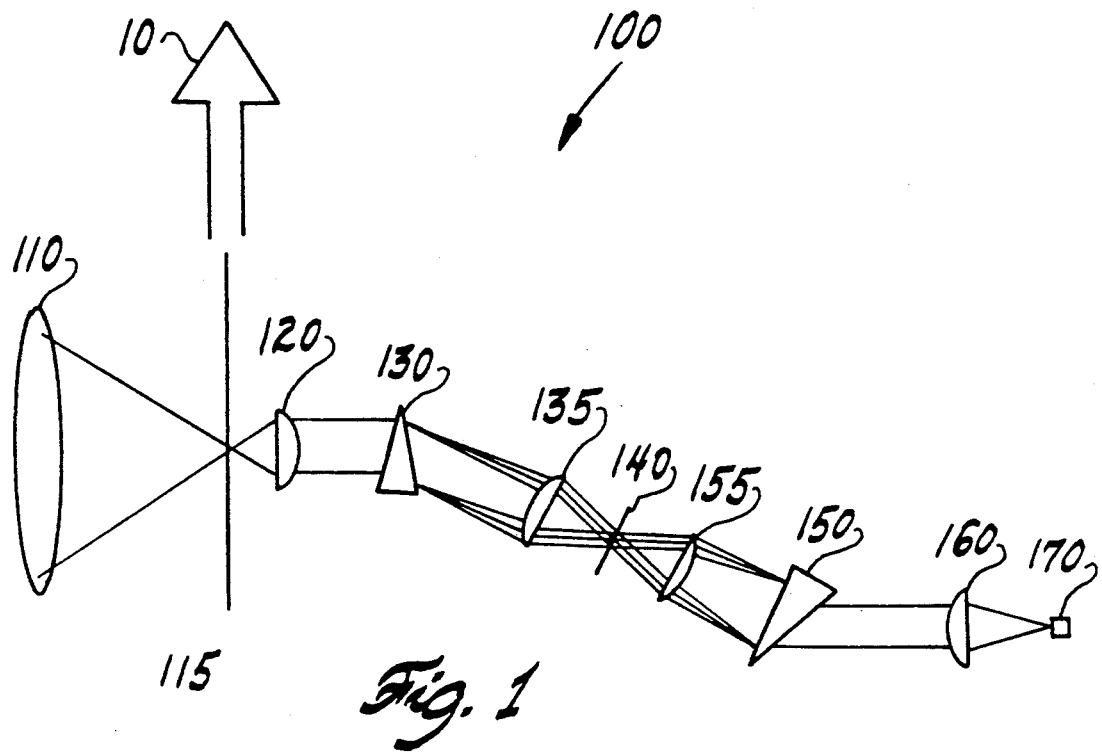
FIG. 1 is a top view of the preferred embodiment of the present invention.

The present invention is an apparatus for producing spectrally weighted output values from received multispectral radiation in real time. The apparatus of the present invention operates to produce spectrally weighted values optically prior to detection of this received radiation. The spectral weights are produced employing weighting filters.

In general the problem of the present invention is to produce a spectrally weighted value 0 in accordance with the following formula:

$$O = \sum_{n=1}^{N} I(\lambda_n) \times W(\lambda_n)$$

where: $I(\lambda_n)$ is the received intensity of radiation within the wavelength band $\lambda_n$ of N possible wavelength bands; and $W(\lambda_n)$ is the weighting factor for the wavelength bans $\lambda_n$. The received intensity $I(\lambda_n)$ is always a positive real number. The weighting factor $W(\lambda_n)$ may be a positive or a negative real value. The number and location of the wavelength bands $\lambda_n$ and the particular weighting factors $W(\lambda_n)$ are selected with reference to the nature of the problem at hand. The one or more spectrally weighted values O permit land use classification, target location or classification, clutter reduction, or the like.

This processing task is difficult or impossible to handle in real time using digital computer processing for many airborne applications where the pixel rate is very high. Further, any practical problem of image processing requires the production of such spectrally weighted values for many image pixels at a high rate. As the number of pixels and the number of such spectrally weighted values desired per pixel increases, the processing task soon outstrips the processing capacity available using current digital computers.

The present invention proposes to perform the sum of products required for production of the spectrally weighted values optically prior to detection of the radiation. In accordance with the present invention the received radiation is dispersed in wavelength using a dispersive element. The dispersive element is preferably a prism or diffraction grating. The dispersive element serves to separate the received radiation by wavelength. This separated radiation can then be processed differently due to the physical separation of the various wavelengths into the desired number of wavelength band area.

The multiplication is carried out through the use of a weighting filter. Each wavelength bin has a weighting filter element. In the preferred embodiment, the transmittance of the particular weighting filter element corresponds to the desired weight factor $W(\lambda_n)$ for that wavelength band. The amount of radiation within a particular wavelength bin which passes through the corresponding transmission filter element is thus the product of the original intensity within that wavelength bin and the transmittance of that filter element It is also feasible to employ reflection filter elements having reflectivities corresponding to the desired weighting factors.

A two filter element technique is employed to achieve bipolar weighting factors. The desired weighting factor $W(\lambda_n)$ is separated into two positive real parts $W^{30}(\lambda_n)$ and $W^{31}(\lambda_n)$, where:

$$W(\lambda_n) = W^{30}(\lambda_n) - W^{31}(\lambda_n)$$

The radiation of each wavelength band area falls on two separate weighting filter elements. A positive weight filter element has a transmittance proportional to $W^{30}(\lambda_n)$. Similarly, a negative weight filter element has a transmittance proportional to $W^{31}(\lambda_n)$.

The apparatus then produces two sums using the half weights $W^+(\lambda_n)$ and $W^-(\lambda_n)$. The sums are produced by converging radiation on a detector. The radiation which passes through the positive weight filter element for each wavelength band area is converged onto a first detector. The radiation which passes through the negative weight filter element for each wavelength band area is converged onto a second detector. This convergence can be achieved by using a wavelength dispersive element in reverse. It is preferable to use the same kind of element employed in the wavelength dispersion, either a prism or a diffraction grating.

The first detector detects the intensity of received radiation. This intensity $O^+$ is given by:

$$O^+ = \sum_{n=1}^{N} I(\lambda_n) \times W^+(\lambda_n)$$

The second detector detects an intensity of radiation $O^-$, given by:

$$O^- = \sum_{n=1}^{N} I(\lambda n) \times W^-(\lambda_n)$$

The final desired spectrally weighted value O is formed by taking the difference between $O^+$ and $O^-$ according to the equation:

$$O = O^+ - O^-$$

This latter subtraction is performed electronically, either in analog circuits or in digital circuits.

The majority of processing required is done optically. Note that the products are formed optically and simultaneously. Also note that the detector outputs are the sums of the desired positive and negative spectrally weighted values. Thus only a single subtraction operation must be formed electronically in order to produce the desired spectrally weighted value. This is well within the processing capability of current digital computer systems to perform in real-time even at the high pixel rate of an airborne sensor.

Figure 2:
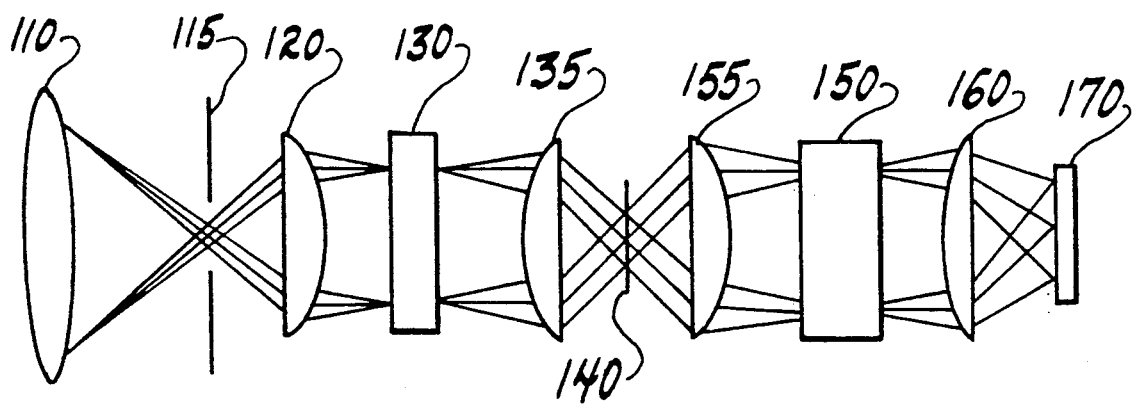
FIG. 2 is a side view of the preferred embodiment of the present invention.

FIGS. 1 and 2 illustrate an embodiment of the optical system in accordance with the present invention. FIG. 1 is a top view and FIG. 2 is a side view. FIG. 1 illustrates the flight path 10 of the platform carrying the sensor system. The sensor system utilizes a sideways looking push broom technique. Lens 110 is the primary optical lens which focusses an image of the desired scene at the plane of image plane mask 115. The radiation passing through image plane mask 115 is collimated by lens 120. Prism 130 is employed as the wavelength dispersion device. Lens 135 focusses radiation from prism 130 at the plane of weighting filter 140. As previously described, weighting filter 140 is employed to form the multiplications required for computation of the spectrally weighted values. FIGS. 1 and 2 illustrate a transmission filter employed as weighting filter 140.

Various configurations of weighting filter 140 will be described below in conjunction with FIGS. 3 to 6. Lens 155 collimates the radiation passing through weighting filter 140. This radiation is recombined in wavelength by converging element 150, which is a prism similar to prism 130. As previously noted, a diffraction grating may also be used for the dispersing element and for the converging element. Lens 160 focusses the recombined radiation upon detector array 170. Detector array 170 includes a plurality of detectors which produce electrical signals corresponding to the intensity of received radiation.

Figure 3:
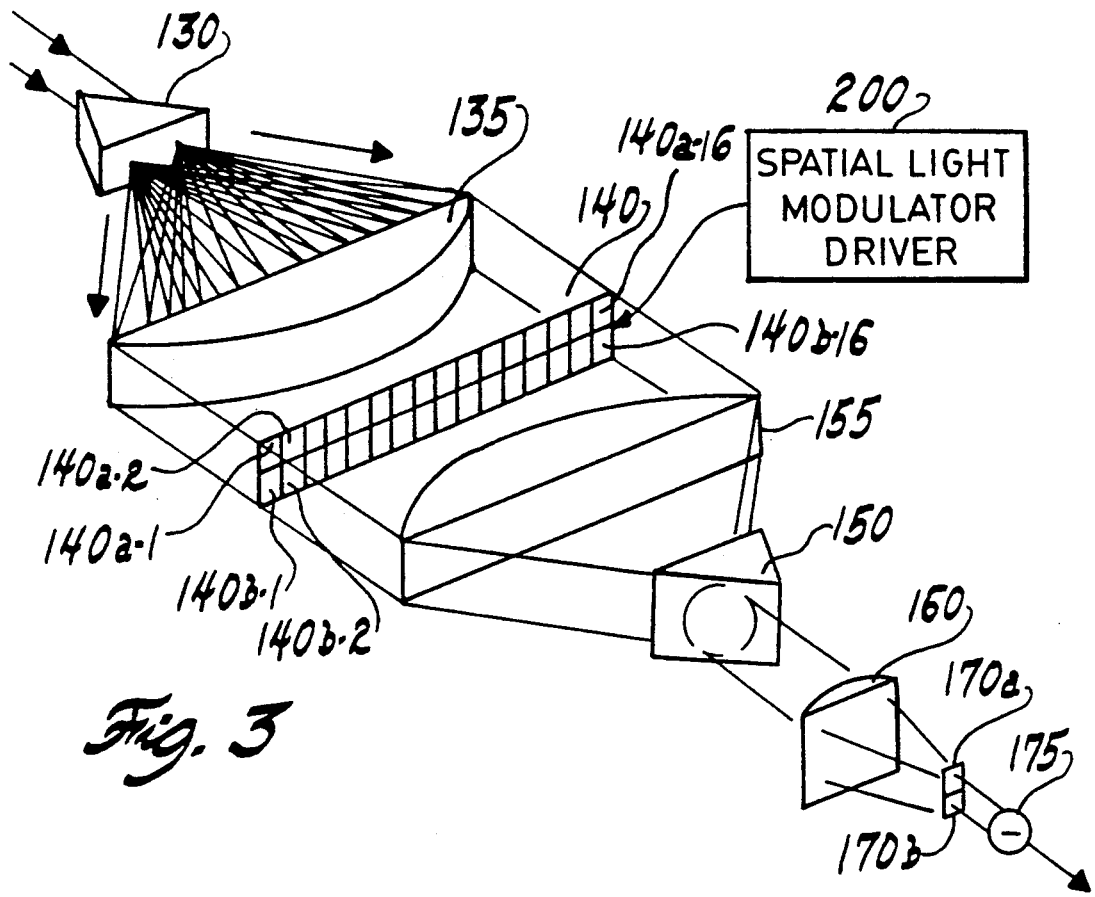
FIG. 3 is a schematic view illustrating the principle of the present invention in an embodiment having a single pixel.

FIG. 3 illustrates an embodiment of the present invention showing a transmission weighting filter in greater detail. The apparatus illustrated in FIG. 3 forms a single spectrally weighted value from the received radiation. Prism 130 receives the radiation from lens 120 (not illustrated in FIG. 3) and disperses this radiation in wavelength. The longer wavelengths appear at one end of lens 135, the shorter wavelengths appear at the other end, with intermediate wavelengths in between. Lens 135 focusses this radiation at transmission filter element 140.

In the apparatus of FIG. 3, weighting filter 140 includes sixteen wavelength band areas. Weighting filter 140 includes sixteen positive weight transmission filter elements $140_{a-1}$ to $140_{a-16}$ and sixteen negative weight transmission filter elements $140_{b-1}$ to $140_{b-16}$. Each positive weight transmission filter element $140_{a-j}$ and its corresponding negative transmission filter element $140_{b-j}$ receive radiation from the j-th wavelength band. The radiation intensity transmitted through each of the positive weight transmission filter elements $140_{a-1}$ to $140_{a-16}$ and through each of the negative weight transmission filter elements $140_{b-1}$ to $140_{b-16}$ of weighting filter 140 depends upon the initial radiation intensity for the particular wavelength band area and the transmittance of the corresponding transmission filter element for that wavelength band area.

The radiation transmitted by weighting filter 140 is recollimated by lens 155. Converging element 150 reassembles the dispersed wavelengths into a single beam. Lens 160 focusses this reassembled radiation upon detector array 170. Detector array 170 includes positive weight detector $170_a$ and negative weight detector $170_b$. Note that the optics including lenses 155 and 160 and converging element 150 insure that radiation that passed through the sixteen positive weight transmission filter elements $140_{a-1}$ to $140_{a-16}$ is directed to and detected by !20 positive weight detector $170_a$. Similarly, radiation that passed through the sixteen negative weight transmission filter elements $140_{b-1}$ to $140_{b-16}$ is directed to and detected by negative weight detector $170_b$. The output of negative weight detector $170_b$ is subtracted from the output of positive weight detector $170_a$ in subtracter 175. The output of subtracter 175 is the desired spectrally weighted value.

Weighting filter 140 may take one of two forms. In the first case, weighting filter 140 may be embodied by a passive filter. This is appropriate in cases where the weights required do not change, that is where the device is to produce a fixed spectrally weighted value. In the second case, weighting filter 140 is embodied by some form of spatial light modulator. FIG. 3 illustrates spatial light modulator driver 200 connected to weighting filter 140. Spatial light modulator driver 200 individually controls the transmittance of the positive weight transmission filter elements $140_{a-1}$ to $140_{a-16}$ and the negative weight transmission filter elements $140_{b-1}$ to $140_{b-16}$. This permits control of the particular spectrally weighted function produced by the apparatus of FIG. 3.

Figure 4:
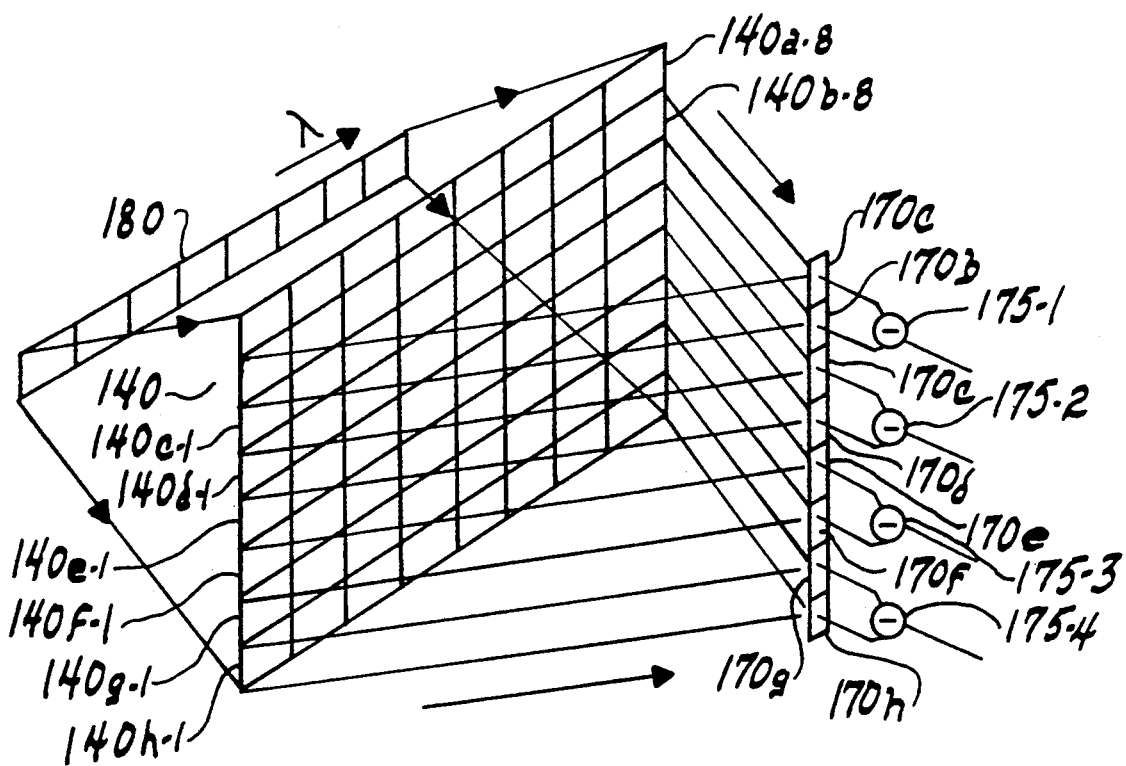
FIG. 4 is a schematic view illustrating the principle of the present invention in an embodiment having multiple functions formed from a single pixel.
Figure 5:
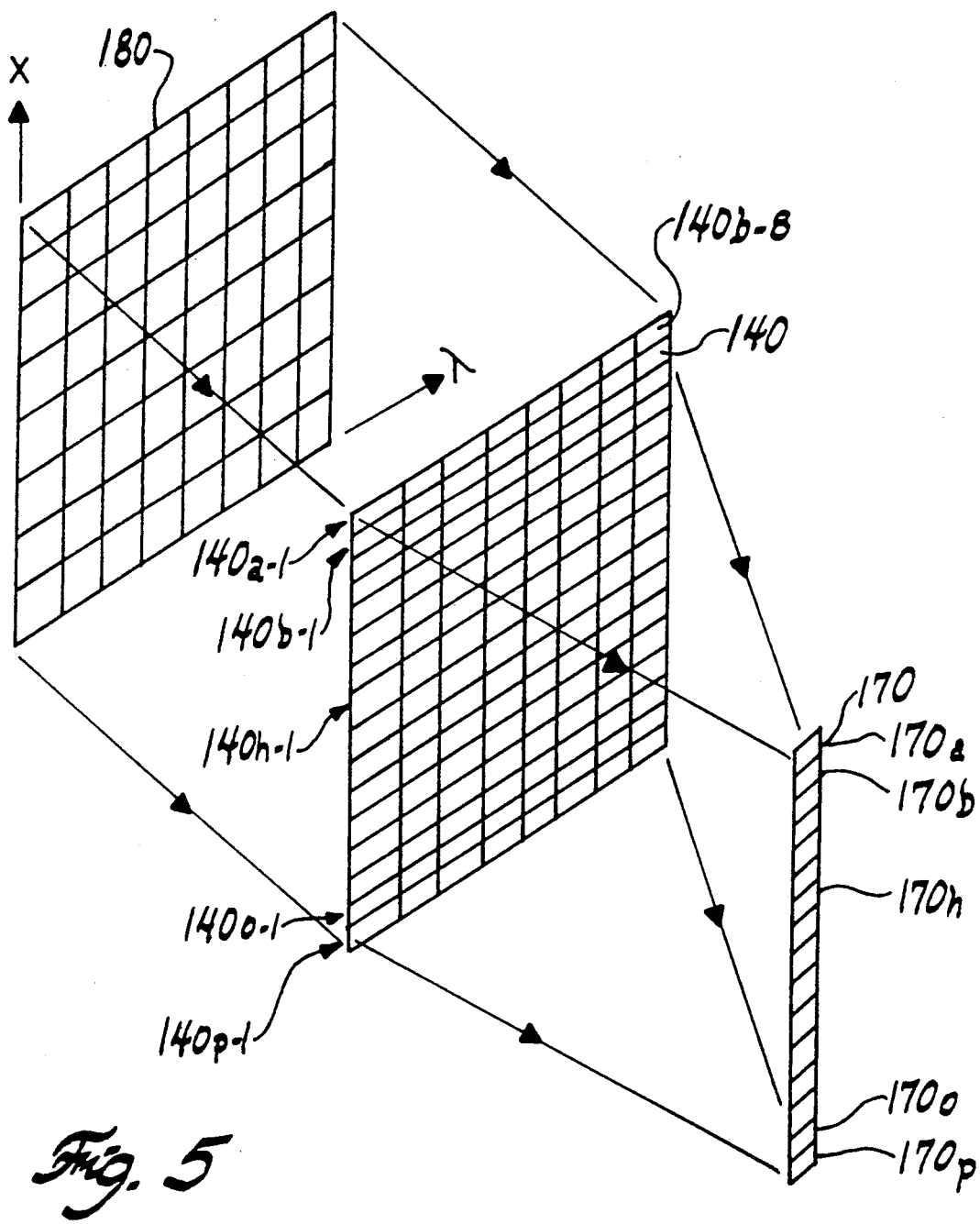
FIG. 5 is a schematic view illustrating the principle of the present invention in an embodiment having a single function formed for each of a plurality of pixels.
Figure 6:
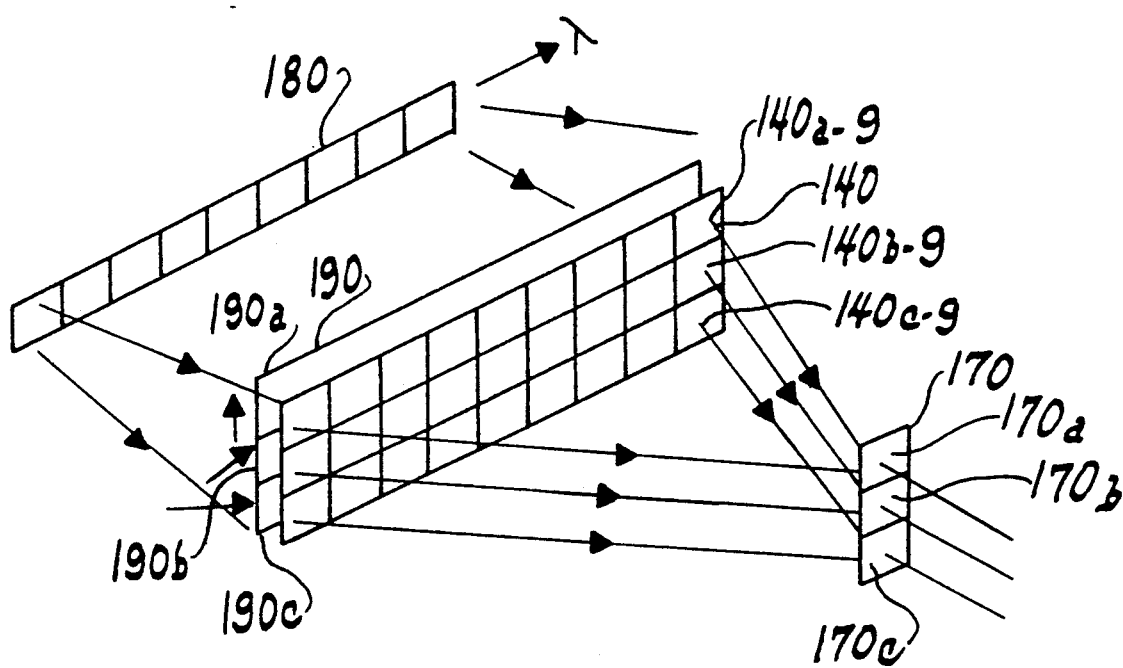
FIG. 6 is a schematic view illustrating the principle of the present invention in an embodiment having spectrally weighted values formed for various polarizations of a single pixel.

FIGS. 4, 5 and 6 illustrate various alternative embodiments of the present invention. These alternative embodiments employ slightly differing radiation dispersions and weighting filters to achieve different results. The apparatus of FIG. 4 simultaneously produces multiple spectrally weighted values from the radiation of a single pixel. The apparatus of FIG. 5 simultaneously produces a single spectrally weighted values from the radiation of each of a plurality of pixels. The apparatus of FIG. 6 simultaneously produces multiple spectrally weighted values for various polarizations from the radiation of a single pixel.

FIG. 4 illustrates schematically an apparatus which produces a plurality of spectrally weighted values from the radiation of a single pixel. Grid 180 illustrates the radiation from a single pixel dispersed in wavelength over eight wavelength band areas in the manner previously described. As illustrated schematically in FIG. 4, this radiation is further dispersed over weighting filter 140 so that plural pairs of weighting filter elements receive radiation from each wavelength band. Weighting filter 140 includes four sets of pairs of positive weight transmission filter elements and negative weight transmission filter elements. The first such pair includes positive weight transmission filter elements $140_{a-1}$ to $140_{a-8}$ and negative weight transmission filter elements $140_{b-1}$ to $140_{b-8}$. The second pair includes positive weight transmission filter elements $140_{c-1}$ to $140_{c-8}$ and negative weight transmission filter elements $140_{d-1}$ to $140_{d-8}$. The third pair includes positive weight transmission filter elements $140_{e-1}$ to $140_{e-8}$ and negative weight transmission filter elements $140_{f-1}$ to $140_{f-8}$. The last pair includes positive weight transmission filter elements $140_{g-1}$ to $140_{g-8}$ and negative weight transmission filter elements $140_{h-1}$ to $140_{h-8}$. These various transmission filter elements may be passive or active in the manner previously described.

Radiation filtered by weighting filter 140 is assembled at detector array 170. Radiation from the eight wavelength bands filtered by the respective transmission filter elements $140_{a-1}$ to $140_{a-8}$ is detected by detector $170_a$. Likewise, radiation filtered by transmission filter elements $140_{b-1}$ to $140_{b-8}$ is detected by detector $170_b$, radiation from transmission filter elements $140_{c-1}$ to $140_{c-8}$ is detected by detector $170_c$, radiation from weight transmission filter elements $140_{d-1}$ to $140_{d-8}$ is detected by detector $170_d$, radiation from transmission filter elements $140_{e-1}$ to $140_{e-8}$ is detected by detector $170_e$, radiation from transmission filter elements $140_{f-1}$ to $140_{f-8}$ is detected by detector $170_f$, radiation from transmission filter elements $140_{g-1}$ to $140_{g-8}$ is detected by detector $170_g$, and radiation from weight transmission filter elements $140_{h-1}$ to $140_{h-8}$ is detected by detector $170_h$.

Subtracters $175_1$ to $175_4$ separately form spectrally weighted values from the received radiation. The output of negative weight detector $170_b$ is subtracted from the output of positive weight detector $170_a$ in subtracter $175_1$. The output of subtracter $175_1$ is one of the desired spectrally weighted values. In the same fashion subtracter $175_2$ forms a second spectrally weighted value from the difference between detectors $170_d$ and $170_c$, subtracter $175_3$ forms a third spectrally weighted value from the difference between detectors $170_f$ and $170_e$, and subtracter $175_4$ forms a fourth spectrally weighted value from the difference between detectors $170_h$ and $170_g$. Thus each detector forms the difference between a pair of positive and negative weight transmission filter elements to form a separate spectrally weighted value. The apparatus of FIG. 4 illustrates the simultaneous formation of a number of spectrally weighted values form the radiation received from a single pixel. The number of such spectrally weighted values which can be simultaneously formed is limited only to the received radiation intensity and the degree to which this received radiation can be divided into the required separate channels.

FIG. 5 illustrates in schematic form an apparatus for simultaneously forming a single spectrally weighted value for each of a plurality of pixels. The task performed by the apparatus of FIG. 5 is the formation of a spectrally weighted value 0 which is a function of pixel location x in accordance with the following formula:

$$O(x) = \sum_{n=1}^{N} I(x, \lambda_n) \times W(x, \lambda_n)$$

where: $I(x, \lambda_n)$ is the received intensity of radiation within the wavelength band $\lambda_n$ for the pixel location x; and $W(x, \lambda_n)$ is the weighting factor for the wavelength band $\lambda_n$ for the pixel location x. This function $O(x)$ is formed in a manner similar to that illustrated in FIG. 4. Grid 180 illustrates radiation from the source dispersed horizontally by wavelength band and vertically by pixel location. Weighting filter 140 includes positive transmission filter elements $140_{a-1}$ to $140_{a-8}$ and negative transmission filter elements $140_{b-1}$ to $140_{a-8}$ corresponding to the respective wavelength band areas of a first pixel location. As previously disclosed, radiation filtered by positive transmission filter elements $140_{a-1}$ to $140_{a-8}$ is detected at detector array 170 by positive detector $170_a$ and radiation filtered by negative transmission filter elements $140_{b-1}$ to $140_{b-8}$ is detected at detector array 170 by negative detector $170_b$. The signals from these two detectors are subtracted by a subtracter (not illustrated in FIG. 5) to form the spectrally weighted value for the first pixel location. In a similar fashion, each other pixel location has a corresponding set of positive and negative transmission filter elements, corresponding positive and negative detectors and a subtracter. In this manner, the apparatus simultaneously forms a spectrally weighted value for each of the plurality of pixels.

FIG. 6 illustrates schematically the manner of simultaneous production of spectrally weighted values for various polarizations of received radiation. It is known in the sensing art that differing structures procedure differing degrees of polarization in their reflected and emitted radiations. In the visible wavelengths where most of the scene illumination comes from the sun, smooth man-made objects tend to reflect light partially polarized parallel to the reflecting surface. Under the same conditions the rough surfaces of natural objects tend to reflect unpolarized light. Knowledge of the direction of illumination would permit extraction of the polarized radiation component for identification of man-made objects. In the microwave region smooth man-made objects tend to be more nearly perfect reflectors and thus reflect unpolarized background illumination from the sky. The water content of natural objects acts as a dielectric filter, and thus these objects reflect polarized microwaves. In the far infrared region the received radiation is due largely to thermal emission rather than reflection. At thermal equilibrium the energy emitted equals the energy absorbed. Thus the energy emitted is the input energy minus the reflected energy. Artificial objects tend to have smooth surfaces which reflect light partially polarized parallel to the surface. The emitted energy thus tends to be polarized in the direction perpendicular to the object surface. Natural object tend to exhibit no such polarization preferences. Thus the polarization of received radiation could be used as a feature in target classification and identification.

FIG. 6 illustrates grid 180 which represents the radiation received from a single pixel dispersed in wavelength. This radiation is filtered by two filters. These are polarization filter 190 and weighting filter 140.

The first filter illustrated in FIG. 6 is polarization filter 190. In the case where the polarization of the desired radiation is known, polarization filter 190 is constructed to favor this known polarization. FIG. 6 illustrates a system in which the polarization of the desired radiation is not known. This would be the case in which the classification apparatus is employed for differing sensing problems. Polarization filter 190 includes three sections $190_a$, $190_b$ and $190_c$ having differing polarization directions. Each of these polarization filter sections $190_a$, $190_b$ and $190_c$ has the same polarization for all the wavelength band areas. As illustrated by the arrows in FIG. 6, polarization filter section $190_a$ has vertical polarization. Polarization filter section $190_b$ has polarization direction disposed at a 120° angle to vertical. Lastly, polarization filter section $190_c$ has a polarization angle of 240°. These three polarization filter section $190_a$, $190_b$ and $190_c$ serve to cover all feasible polarizations. It is equally feasible to include either two, four or more polarization filter sections, each having differing polarizations covering the range of possible polarizations. The limit on the number of such filter sections is the original radiation intensity and the amount of radiation which can be directed to each polarization section.

Weighting filter 140 is disposed in tandem with polarization filter 190. The particular order of these filters is immaterial, they need only be disposed in tandem. Weighting filter 140 includes: transmission weighing filter elements $140_{a-1}$ to $140_{a-9}$ corresponding to polarization filter section $190_a$; transmission weighing filter elements $140_{b-1}$ to $140_{b-9}$ corresponding to polarization filter section $190_b$; and transmission weighing filter elements $140_{c-1}$ to $140_{c-9}$ corresponding to polarization filter section $190_c$. Weighting filter 140 thus includes a transmission filter elements for each wavelength band area for each polarization filter section. As previously described, the various transmission filter elements of weighting filter 140 may be passive filters or active filters.

The radiation filtered by polarization filter 190 and weighting filter 140 is converged on detector array 170. FIG. 6 illustrated detector array 170 including detectors $170_a$, $170_b$ and $170_c$. Detector $170_a$ detects the converged radiation filtered by polarization filter element $190_a$ and transmission weighting filter elements $140_{a-1}$ to $140_{a-9}$. Detector $170_b$ detects radiation filtered by polarization filter element $190_b$ and transmission weighting filter elements $140_{b-1}$ to $140_{b-9}$. Detector $170_c$ detects radiation filtered by polarization filter element $190_c$ and transmission weighting filter elements $140_{c-1}$ to $140_{c-9}$. The outputs of detectors $170_a$, $170_b$ and $170_c$ form the desired spectrally weighted values for various polarizations.

I claim:

1. An apparatus for forming a spectrally weighted value from multispectral radiation received from a pixel comprising:

an optical system for gathering multispectral radiation from the pixel;

a wavelength dispersing element disposed in a plane to receive the multispectral radiation gathered by said optical system for spatially disbursing said gathered radiation by wavelength into a plurality of wavelength band areas;

a weighting filter disposed in a plane to receive radiation dispersed by said wavelength dispersing element having a first weighting filter element and a second weighting filter element for each of said wavelength band areas;

a wavelength converging element disposed to receive radiation filtered by said weighting filter for spatially converging all wavelengths of radiation filtered by said first weighting filter elements to a first detector location and all wavelengths of radiation filtered by said second weighting filter elements to a second detector location;

a first detector disposed at said first detector location for forming a first electrical signal corresponding to the intensity of radiation at said first detector location;

a second detector disposed at said second detector location for forming a second electrical signal corresponding to the intensity of radiation at said second detector location; and a difference device connected to said first and second detectors for forming a difference signal between said first and second electrical signals, said difference signal being the spectrally weighted value.

2. The apparatus as claimed in claim 1, wherein:

said weighting filter consists of a passive transmission filter having a fixed transmittance for said first and second transmission filter elements for each of said plurality of wavelength band areas.

3. The apparatus as claimed in claim 1, wherein:

said weighting filter consists of a spatial light modulator having controllable transmittance for said first and second weighting filter elements for each of said plurality of wavelength band areas.

4. The apparatus as claimed in claim 1, wherein:

said wavelength dispersing element and said wavelength converging element each include a prism.

5. The apparatus as claimed in claim 1, further comprising:

a first lens system disposed between said wavelength dispersing element and said weighting filter for focussing radiation received from said wavelength dispersing element at the plane of said weighting filter; and a second lens system disposed between said weighting filter and said wavelength converging element for collimating radiation received from said weighting filter.

6. An apparatus for forming a plurality of spectrally weighted values from multispectral radiation received from a pixel comprising:

an optical system for gathering multispectral radiation from the pixel;

a wavelength dispersing element disposed to receive the multispectral radiation gathered by said optical system for spatially disbursing said gathered radiation by wavelength into a grid of a plurality of wavelength band areas.

a weighting filter disposed to receive radiation dispersed by said wavelength dispersing element having a plurality of pairs of first and second weighting filter elements corresponding to each of said wavelength band areas;

a wavelength converging element disposed to receive radiation filtered by said weighting filter for spatially converging all wavelengths of radiation filtered by said first weighting filter elements to a first detector location and all wavelengths of radiation filtered by said second weighting filter elements to a second detector location;

a plurality of first detectors, one disposed at each first detector location, each first detector for forming a first electrical signal corresponding to the intensity of radiation at said corresponding first detector location;

a plurality of second detectors, one disposed at each second detector location, each second detector for forming a second electrical signal corresponding to the intensity of radiation at said corresponding second detector location; and a plurality of difference devices each connected to corresponding first and second detectors, each difference device for forming a difference signal between said corresponding first and second electrical signals, said difference signals being the spectrally weighted values.

7. The apparatus as claimed in claim 6, wherein:
said weighting filter consists of a passive transmission filter having a fixed transmittance for each of said plurality of pairs of first and second weighting filter elements for each of said plurality of wavelength band areas.

8. The apparatus as claimed in claim 6, wherein:
said weighting filter consists of a spatial light modulator having controllable transmittance for each of said plurality of pairs of first and second weighting filter elements for each of said plurality of wavelength band areas.

9. An apparatus for forming a spectrally weighted value from multispectral radiation received from each of a plurality of pixels comprising:

an optical system for gathering multispectral radiation from each of said plurality of pixels into a linear array;

a wavelength dispersing element disposed to received the multispectral radiation gathered by said optical system for spatially dispersing said gathered radiation by wavelength for each of said plurality of pixels into a plurality of wavelength band areas;

a weighting filter disposed to receive radiation dispersed by said wavelength dispersing element having first and second weighting filter elements corresponding to each of said wavelength band areas;

a wavelength converging element disposed to receive radiation filtered by said weighting filter for spatially converging all wavelengths of radiation filtered by each of said first weighting filter elements to a corresponding first detector location and all wavelengths of radiation filtered by each of said second weighting filter elements to a corresponding second detector location;

a plurality of first detectors, one disposed at each first detector location, each first detector for forming a first electrical signal corresponding to the intensity of radiation at said corresponding first detector location;

a plurality of second detectors, one disposed at each second detector location, each second detector for forming a second electrical signals corresponding to the intensity of radiation at said corresponding second detector location; and a plurality of difference devices connected to corresponding first and second detectors, each difference device for forming a difference signal between corresponding first and second electrical signals said difference signals being the spectrally weighted value.

10. The apparatus as claimed in claim 9, wherein:
said weighting filter consists of a passive transmission filter having a fixed transmittance for said first and second weighting filter elements for each of said plurality of wavelength band areas for each of said plurality of pixels.

11. The apparatus as claimed in claim 9, wherein:
said weighting filter consists of a spatial light modulator having controllable transmittance for said first and second weighting filter elements for each of said plurality of wavelength band areas for each of said plurality of pixels.

* * * * *

UNITED STATES PATENT AND TRADEMARK OFFICE
CERTIFICATE OF CORRECTION

PATENT NO. : 5,090,807

DATED : February 25, 1992

INVENTOR(S) : Tai

It is certified that error appears in the above-identified patent and that said Letters Patent is hereby corrected as shown below:

Column 3, line 9, delete "wavelength areas" and insert --wavelength band areas--;

Column 4, line 24, delete "bans" and insert --band--;

Column 4, line 55, delete "area" and insert --areas--;

Column 4, line 57, delete "bin" and insert --band area--;

Column 4, line 62, delete "bin" and insert --band area--;

Column 4, line 65, delete "bin" and insert --band area--;

Column 4, line 65, delete "element It" and insert --element. It--;

Column 5, line 4, delete "$W^{30}(\lambda_n)$ and $W^{31}(\lambda_n)$" and insert --$W^{+}(\lambda_n)$ and $W^{-}(\lambda_n)$--;

Column 5, line 5, delete "$W(\lambda_n)=W^{30}(\lambda_n)-W^{31}(\lambda_n)$" and insert --$W(\lambda_n)=W^{+}(\lambda_n)-W^{-}(\lambda_n)$--;

Column 5, line 9, delete "$W^{30}$" and insert --$W^{+}$--;

Column 5, line 11, delete "$W^{31}$" and insert --$W^{-}$--;

UNITED STATES PATENT AND TRADEMARK OFFICE
CERTIFICATE OF CORRECTION

PATENT NO. : 5,090,807

DATED : February 25, 1992

INVENTOR(S) : Tai

It is certified that error appears in the above-identified patent and that said Letters Patent is hereby corrected as shown below:

Column 6, line 51, delete "!20 positive" and insert --positive--;

Column 7, line 35, delete "$140_{a-8}$" and insert --$140_{d-8}$--;

Column 7, line 52, delete "$170_a$," and insert --$170_d$,--;

Column 8, line 35, delete "$140_{a-8}$" and insert --$140_{b-8}$--;

Column 12, line 4, delete "received" and insert --receive--.

Signed and Sealed this

Fourth Day of August, 1992

Attest:

DOUGLAS B. COMER

Attesting Officer

Acting Commissioner of Patents and Trademarks